(12) United States Patent
Prevrhal et al.

(10) Patent No.: US 9,332,952 B2
(45) Date of Patent: May 10, 2016

(54) DATA-DRIVEN OPTIMIZATION OF EVENT ACCEPTANCE/REJECTION LOGIC

(71) Applicant: KONINKLIJKE PHILIPS N.V., Eindhoven (NL)

(72) Inventors: Sven Prevrhal, Hamburg (DE); Eberhard Sebastian Hansis, Hamburg (DE); Jason Stephen Wiener, Fremont, CA (US); Joerg Bredno, San Francisco, CA (US); David Sowards-Emmerd, San Jose, CA (US); Lingxiong Shao, Saratoga, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 110 days.

(21) Appl. No.: 14/348,908

(22) PCT Filed: Oct. 3, 2012

(86) PCT No.: PCT/IB2012/055297
§ 371 (c)(1),
(2) Date: Apr. 1, 2014

(87) PCT Pub. No.: WO2013/050941
PCT Pub. Date: Apr. 11, 2013

(65) Prior Publication Data
US 2014/0257096 A1 Sep. 11, 2014

Related U.S. Application Data

(60) Provisional application No. 61/543,835, filed on Oct. 6, 2011.

(51) Int. Cl.
*A61B 6/00* (2006.01)
*G01T 1/29* (2006.01)
(Continued)

(52) U.S. Cl.
CPC ............ *A61B 6/5205* (2013.01); *A61B 6/037* (2013.01); *A61B 6/0407* (2013.01); *A61B 6/469* (2013.01);
(Continued)

(58) Field of Classification Search
CPC ...... A61B 6/037; A61B 6/0407; A61B 6/469; A61B 6/481; A61B 6/5205; A61B 6/5294; A61B 6/544; A61B 6/547; A61K 2121/00; A61K 2123/00; A61K 51/00; G01T 1/2985
See application file for complete search history.

(56) References Cited

U.S. PATENT DOCUMENTS

| | | | |
|---|---|---|---|
| 4,755,679 | A | 7/1988 | Wong |
| 6,346,706 | B1 | 2/2002 | Rogers et al. |

(Continued)

FOREIGN PATENT DOCUMENTS

WO 2007082126 A2 7/2007

OTHER PUBLICATIONS

Conti, M.; Tailoring PET Time Coincidence Window Using CT Morphological Information; 2007; IEEE Trans. on Nuclear Science; 54(5)1599-1605.
(Continued)

*Primary Examiner* — Mark Remaly

(57) ABSTRACT

In Positron Emission Tomography, a time window (260) and an energy window (225) are dynamically adjusted, based on an attenuation map, count rate, clinical application, discrimination tailoring, and/or offline discrimination tailoring. Detected radiation events are filtered using the dynamically adjusted energy and time windows into scattered events, random events, and true events. The true events are input to image reconstruction, correction, and error analysis.

15 Claims, 6 Drawing Sheets

(51) Int. Cl.
*A61B 6/04* (2006.01)
*A61K 51/00* (2006.01)
*A61B 6/03* (2006.01)

(52) U.S. Cl.
CPC ........... *A61B 6/481* (2013.01); *A61B 6/5294* (2013.01); *A61B 6/544* (2013.01); *A61B 6/547* (2013.01); *A61K 51/00* (2013.01); *G01T 1/2985* (2013.01); *A61K 2121/00* (2013.01); *A61K 2123/00* (2013.01)

(56) References Cited

U.S. PATENT DOCUMENTS

| | | | |
|---|---|---|---|
| 7,473,900 | B2 | 1/2009 | Vija |
| 7,626,171 | B2 * | 12/2009 | Cooke ............... A61B 6/037 250/363.03 |
| 2004/0015075 | A1 * | 1/2004 | Kimchy ............. A61B 6/4258 600/424 |
| 2004/0030246 | A1 | 2/2004 | Townsend et al. |
| 2006/0284098 | A1 | 12/2006 | Vija |
| 2011/0064293 | A1 | 3/2011 | Takayama et al. |
| 2011/0129132 | A1 * | 6/2011 | Tsukerman ......... A61B 5/055 382/128 |

OTHER PUBLICATIONS

Fontaine, R., et al.; Architecture of a Dual-Modality, High-Resolution, Fully Digital Positron Emission Tomography/Computed Tomography (PET/CT) Scanner for Small Animal Imaging; 2005; IEEE Trans. on Nuclear Science; 52(3)691-696.

Jones, W. F., et al.; Optimizing Rod Window Width in Positron Emission Tomography; 1995; IEEE Trans. on Medical Imaging; 14(2)266-270.

Kao, C-M, et al.; A High-Sensitivity Small-Animal PET Scanner: Development and Initial Performance Measurements; 2009; IEEE Trans. on Nuclear Science; 56(5)2678-2688.

Kao, C-M, et al.; Initial performance evaluation of a modular, large-area detector PET scanner for small animal imaging; 2005; IEEE Nuclear Science Symposium Record; vol. 4:2081-2084.

McElroy, D. P., et al.; Singles list mode data processing for MADPET-II; 2004; IEEE Nuclear Science Symposium Conference Record; vol. 5:3325-3329.

Tetrault, M-A., et al.; System Integration of the LabPET Small Animal PET Scanner; 2006; IEEE Nuclear Science Symposium Record; M06-100:1880-1884.

Wang, C., et al.; A Real Time Coincidence System for High Count-rate TOF or Non-TOF PET Cameras Using Hybrid Method Combining AND-logic and Time-mark Technology; 2009; IEEE MPSS Real Time Conference; RTSA3-5:321-325.

Yang, Y., et al.; Observations Regarding Scatter Fraction and NEC Measurements for Small Animal PET; 2006; IEEE Trans. on Nuclear Science; 53(1)127-132.

* cited by examiner

DATA-DRIVEN OPTIMIZATION OF EVENT ACCEPTANCE/REJECTION LOGIC

CROSS REFERENCE TO RELATED APPLICATIONS

This application is a national filing of PCT application Serial No. PCT/IB2012/055297, filed Oct. 3, 2012, published as WO 2013/050941 A2 on Apr. 11, 2013, which claims the benefit of U.S. provisional application Ser. No. 61/543,835 filed Oct. 6, 2011, which is incorporated herein by reference.

The present application relates to Nuclear medicine imaging, Positron Emission Tomography (PET), Single Photon Emission Computed Tomography (SPECT), and specifically to determination of events used to reconstruct PET images.

PET nuclear medicine involves the introduction of a radiopharmaceutical in the body of a subject. The radiopharmaceuticals target specific areas of interest or organs through metabolic processes. The radiopharmaceuticals decay with a relatively short half-life. The base process for image formation are decay events that result in a positron being emitted. The positron travels a short distance before striking an electron. When the positron strikes the electron, an annihilation event occurs. An annihilation event is marked by the emission of two gamma photons of energy at 511 keV which travel in 180° opposite directions. The path traveled by photons in opposite directions is called the line-of-response (LOR).

A PET scanner detects the pairs of gamma photons from a common annihilation event which are called coincidence events. A PET scanner discriminates between the coincidence events and scattered or random events. A scattered event is an event in which the path of a photon is altered, typically due to Compton scattering by a dense material. The probability of scattering varies with the patient size, density of various types of tissue such as bone, and other objects present such as implants. When the path is altered, the photon loses energy and arrives with less than 511 keV in energy. In Compton scattering the angle of scattering (Compton angle) is proportional to the lost energy. The larger the energy window, the greater the Compton scattering angle that is permitted.

A random event occurs when only one of a pair of photons strikes a detector. The other photon either travels outside the area covered by the detectors or is entirely absorbed by interaction with a nucleus or the like. A single random event is not used because both events of a pair are needed to calculate the LOR used in the reconstruction algorithm. The time interval for a gamma photon to travel from one detector to a diametrically opposing detector represents the maximum interval between coincidence events.

Due to detector physics and unavoidable imprecision of photon energy and arrival time measurement, the time interval for acceptable coincidence events cannot be set arbitrarily small. The time interval includes both the travel time and delays or differences in measuring time. As imprecision in time measurement is reduced, time of flight measurements can be made and become more accurate. However, time differences between individual detector measurements, precise time measurement, and variations due to operating conditions still contribute to the imprecision of event times. Larger time windows or longer acceptable intervals between events which are coincident allow for greater imprecision in the detected LORs.

Similarly, the difference of a measured energy level of an event and the expected energy 511 keV of a gamma photon emitted from an annihilation event cannot be arbitrarily small. Particular technologies used in detectors, operating temperatures, and other imprecision combine to vary the measured energy level of an event.

The number of detected coincidence events varies with the number of annihilation events occurring. The number of annihilation events is determined by the type of radiopharmaceutical used, and the concentration of the radiopharmaceutical in the detection region. The type of radionuclide in the radiopharmaceutical has a known half-life or decay rate. As the radionuclides decay, the concentration of the radiopharmaceutical decreases as does the count rate. The radiopharmaceutical is configured to target selected metabolic processes which uptake or absorb the radiopharmaceutical to create concentrated areas or bright spots in the image. The radiopharmaceutical washes out of target areas or target organs at different rates as the radionuclide decays, the pharmaceutical is metabolized or the like. The concentration of a radiopharmaceutical affects the emission rate. For example, Rubidium-82 chloride targets cardiac muscle cells. It has a high emission rate and a short half life of 75 seconds.

Discrimination of events can be greater with very high emission rates while still recording enough coincidence events to reconstruct quality images. Alternatively discrimination of events can be lessened with lower emission rates in order to obtain more coincidence events.

Without precise time of flight information, image reconstruction can use a statistical distribution of expected points of emission. A statistical method uses a small sample set before computing a center or distribution. Hardware parameters for determining a coincidence event are typically set by the manufacturer, and are not accessible for modification by an operator. Two parameters are set: a time window which determines the maximum permitted interval between events for coincidence, and the minimum energy level required for a straight, non-scattered LOR event. There is a trade-off between sensitivity to true events and false acceptance of spurious events. Spurious events include strikes of photons at detectors which are not pairs emitted from the same annihilation event and include random and scattered events.

There is information known prior to data acquisition and data available during data acquisition which can be used to tailor time and energy windows. Characteristics of radiopharmaceuticals are known such as the area or organ targeted, expected emission rates, and the half life. Time-dosage information is known prior to data acquisition. Patient size and regions of interest are known prior to data acquisition. Computed-tomography or magnetic resonance attenuation correction maps obtained on hybrid devices provide detailed information about tissue density for a particular subject such as where dense bones are found and where high concentrations of water equivalent tissues exist.

The present application provides a new and improved data-driven acceptance of coincidence events which overcomes the above-referenced problems and others.

In accordance with one aspect, a method of Positron Emission Tomographic imaging determines a time window (260) and an energy window (225). The coincident radiation event pairs are selected with the energy and time window. The selected coincident pairs are reconstructed into an image representation. The time window and/or the energy window are dynamically adjusted during at least one of event acquisition or image reconstruction.

In accordance with another aspect, a method of Positron Emission Tomographic imaging receives an event at a detector. The event is recorded in an event list. The event list is filtered after data acquisition for coincidence event pairs. An image is reconstructed from the filtered event list using a reconstruction processor. The filter window is dynamically adjusted for time and/or energy windows.

In accordance with another aspect, a Positron Emission Tomography system includes an array of radiation detectors, a coincidence processing unit, an electronic memory, and a reconstruction processor. An array of radiation detectors generate output signals in response to receiving radiation. A coincidence processing unit determines coincident pairs. An electronic memory records coincident pairs. A reconstruction processor reconstructs images from the event list and dynamically adjusts windows.

One advantage is that time and/or energy windows for acceptance of coincidence events can be adjusted with known data prior to data acquisition.

Another advantage is that time and/or energy windows for acceptance of coincidence events can be dynamically adjusted during data acquisition based on feedback.

Another advantage is that the number of coincidence events recorded is increased.

Another advantage is the improvement in image quality of PET images due to the improvement in data quality used to reconstruct images.

Another improvement is the recording of event information used to analyze errors.

Still further advantages of the present invention will be appreciated to those of ordinary skill in the art upon reading and understanding the following detailed description.

The invention may take form in various components and arrangements of components, and in various steps and arrangements of steps. The drawings are only for purposes of illustrating the preferred embodiments and are not to be construed as limiting the invention.

Figure 1:
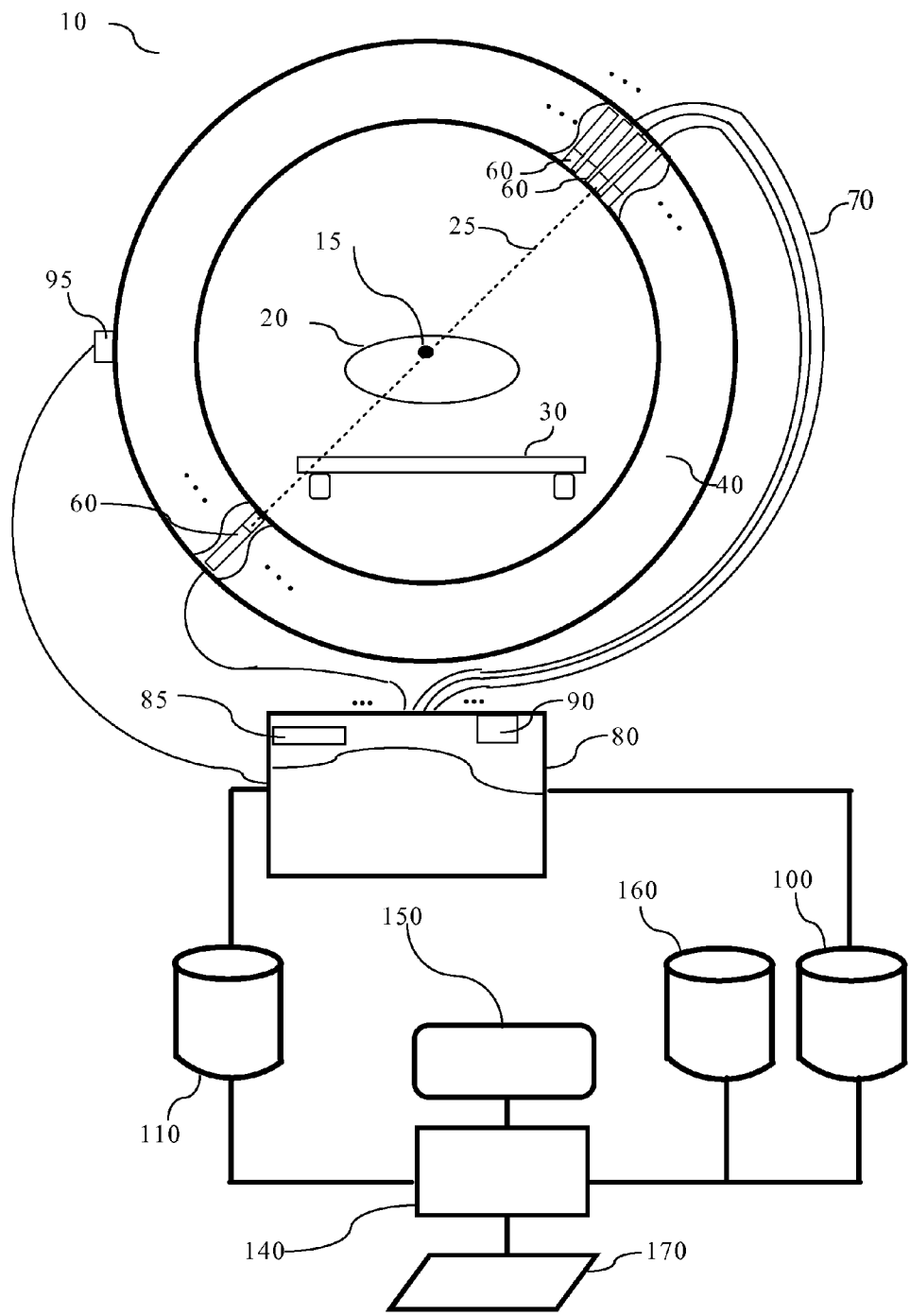
FIG. 1 is a diagram of a PET scanner system with cutaways revealing the components used during the data driven data acquisition process.

With reference to FIG. 1, a PET scanner 10 detects positron emission events. A location of an annihilation event 15 occurs within a subject, targeted organ, or region of interest 20. The subject is placed on an exam table 30 which moves through a detector array 40. The detector array 40 is typically shaped as a ring inside the gantry 30 with rows of detectors 60 extending longitudinally. The detectors 60 receive gamma photons and transmit pulses of electricity on wiring circuits 70 when a gamma photon strikes. An example of a detector is a scintillator crystal connected to a photomultiplier tube, a photodiode, a silicon photomultiplier (SiPM), or the like. The amplitude of the pulse reflects the energy of the photon received. Using an analog to digital converter, if the photodetector is not digital, a clock circuit adds a time stamp, and a detector circuit adds an identification or location of the detecting detector to form a digital data packet for each detected event. The wiring circuits 70 connect the individual detectors to a coincidence processing unit 80.

In one embodiment, the coincidence processing unit 80 retrieves from memory 100 the time and energy window settings as a function of time and/or table 30 position to be used during data acquisition. The settings are stored in a memory 100 with a system matrix file which specifies the operating environment for the system. The coincidence processing unit 80 receives event data and places the event data in a temporary memory such as a buffer 85. As events are received the coincidence processing unit uses the time and energy window settings in effect for that table position to determine whether pairs of events comprise a coincidence event. If a pair of events meets the energy and time window settings, the pair is accepted as a coincidence pair. A coincidence pair defines a LOR 25 between the detectors which detected the pair of events. As the table 30 makes discrete or continuous shifts, the coincidence processing unit 80 uses the time and energy window settings 100 corresponding to the current table position. Alternatively, an elapse of a time such as the passing of a selected fraction of the half-life, causes a change in window settings.

In another embodiment, the windowing parameters are adjusted dynamically during the data acquisition process based on feedback from the detected data. The coincidence processing unit 80 maintains a counter or counting circuit 90 of a current rate at which events are being received. When the count rate is high, windowing parameters are narrowed. When the count rate is low, windowing parameters are widened. In other embodiments windowing parameters are adjusted based on current operating temperature, or a shift in the maximum energy of events. One or more temperature sensors 95 mounted on the detector array provide additional feedback to the coincidence processing unit 80. In another embodiment, the windowing parameters are adjusted based on an amount of scattered or spurious events.

As events are paired and determined to be coincident by the coincidence processing unit 80, the event pair is logged to an event list memory 110. The event list memory 110 records the event time, energy level, detection location and changes in window settings.

In a prospective embodiment, the reconstruction processor 140 reads the coincidence event list memory 110 and reconstructs an image. The image is displayed on a display 150 or alternatively stored for later access.

In a retrospective embodiment, all event pairs are within preselected windows, which removes noise, unacceptable scatter and the like, and are stored in the list memory 110. The reconstruction processor 140 decides which coincident pairs to reconstruct based at least on the time and energies of each event, such that the reconstruction process sets the time and energy during reconstruction. The relative detection times of the events of the coincident pair can be used to determine time-of-flight (TOF) information and a TOF reconstruction is performed. In the retrospective embodiments, an image can be constructed with initial time and energy windows. Based on characteristics of the image or the like, the image can be reconstructed again using events with meet more restrictive time and/or energy window requirements.

The patient size is input or selected using an input device 170 and/or stored lists. The target organ or region of interest is input or selected. Information about the radiopharmaceutical is input or selected such as the type of radiopharmaceutical, the time the radiopharmaceutical was administered to the subject and the dosage administered. Information stored with the type of radiopharmaceutical includes half-life, and emission rates. An attenuation map (AC map) for the patient is typically, e.g. using computed tomography, generated prior to the PET imaging and used in the PET reconstruction. The AC map provides information about the relative densities and expected scatter to be encountered by different regions during data acquisition. The processor inputs this information and outputs corresponding time and energy windowing parameters stored. In one embodiment, the windows are adjusted based on the density of tissue lying along each defined LOR.

In another embodiment, the windows are adjusted to improve the count rate in some regions and LOR accuracy in other regions to optimize sensitivity in some regions of the reconstructed image and resolution in others.

Figure 2:
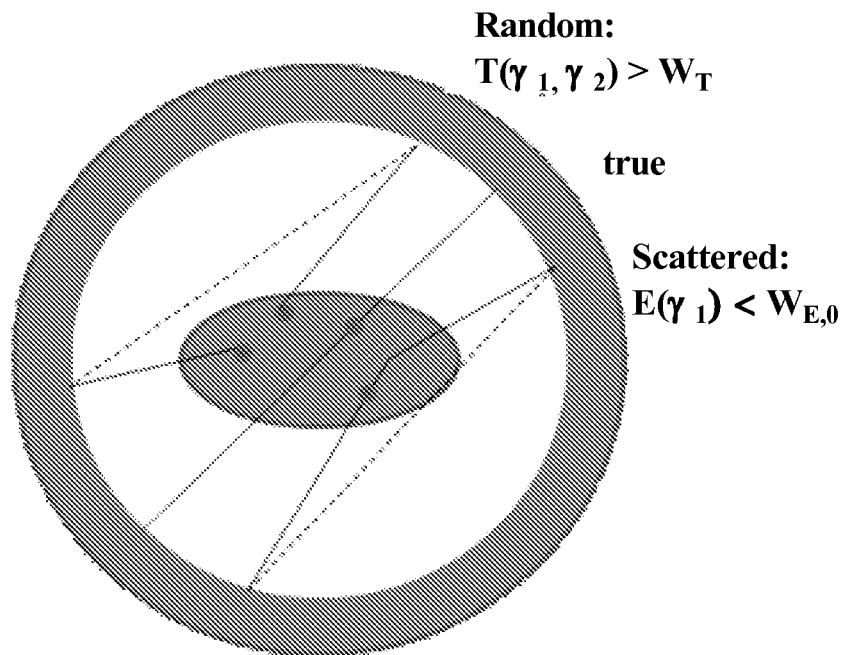
FIG. 2 is a diagram illustrating random, scattered, and true events.

With reference to FIG. 2, events are classified as random, true, or scattered. Random events are determined when the time interval, T between events $\gamma_1$ and $\gamma_2$ detected is greater than a set time window $W_T$. When the interval between two detected events is sufficiently large, two separate radionuclide decay events must have produced the detected photon events. For some random events a LOR does not pass through the subject. In true events, the LOR between the detectors passes through the point of emission. Scattered events occur due to Compton scattering. The greater the Compton or scatter angle, the greater the energy loss. Scattered events are discriminated by their energy level. An event, $\gamma_1$, is scattered when the measured energy level is less than a set amount $W_{E,0}$, e.g. 511 keV. The LOR for a scattered event pair $\gamma_1$, $\gamma_2$ is not a straight line through the emission point. However, if the scatter angle is very small, the LOR deviates very little from the straight line through the emission point and can be used with minimal effect on resolution and accuracy. In the diagram solid lines are true paths, while dotted lines represent the false LORs.

Figure 3:
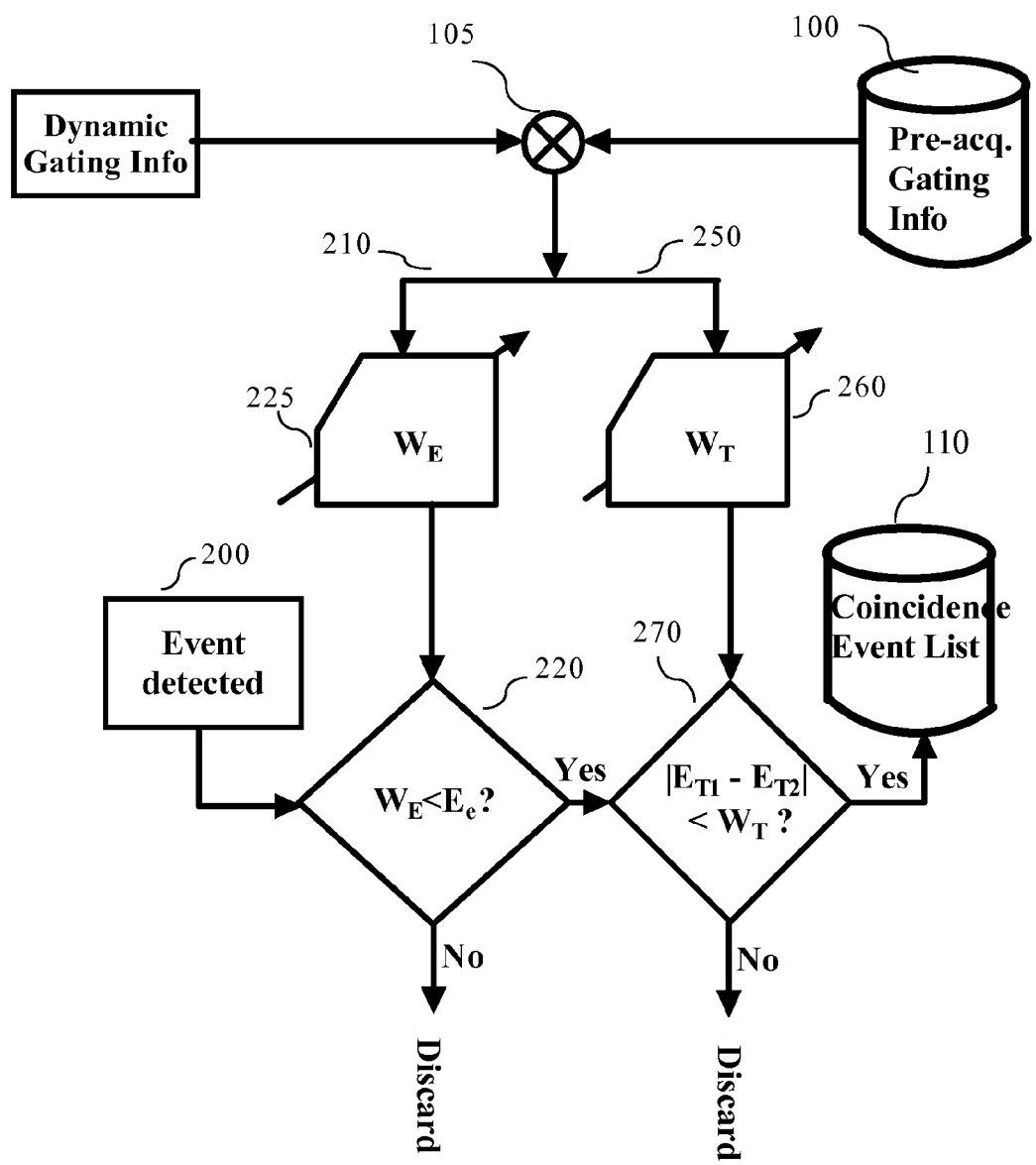
FIG. 3 is a diagram illustrating the data acquisition process.

With reference to FIG. 3, the coincidence processing unit 80 retrieves the time and energy window parameters stored in memory 100 by the processor 140 prior to data acquisition, input by the clinician, or dynamically calculated by the processor. This information includes time and energy window parameters by table 30 position and/or time information (e.g. based on half-life), and/or target and radio pharmaceutical characteristics based on inputs from a lookup table 160. The energy window parameter(s) 225 and the time window parameter 260 are dynamically adjusted 105 by the coincidence processor 80 based on feedback from a counter 90, temperature sensor 95, etc.

As events are detected 200, energy windowing is applied. The energy window 220 sets a minimum energy level 225 permitted of an event to be designated a part of a coincidence pair. Alternatively, the energy window 220 includes both a minimum and a maximum to allow for errors in energy measurement. If the event does not pass the window 220 for the energy level, the event is discarded. $W_E < E_e$, where $W_E$ is the energy window as a function of table position and/or time including dynamic adjustments, and $E_e$ is a measured energy level e. A maximum value of measured energy $W_{E,max}$ may be used for the energy window, $W_{E,min} < E_e < W_{E,max}$, otherwise the maximum of 511 keV is used.

Events passing the energy window 220 are paired with another event as a coincidence pair. The event pairs must pass a time window 270. The time window 270 is a maximum time interval between detected events for the event to be considered coincidence 260. $|E_{T1} - E_{T2}| < W_T$, where $W_T$ 260 is the time window 270 parameter as a function of table position and/or time including dynamic adjustments, $E_{T1}$ is a detected event at time T1, and $E_{T2}$ is a detected event at time T2. If the coincidence pair passes the time window 270 then it is recorded as a coincidence pair in the coincidence event list 110. If it does not pass the time window then it is discarded.

Figure 4:
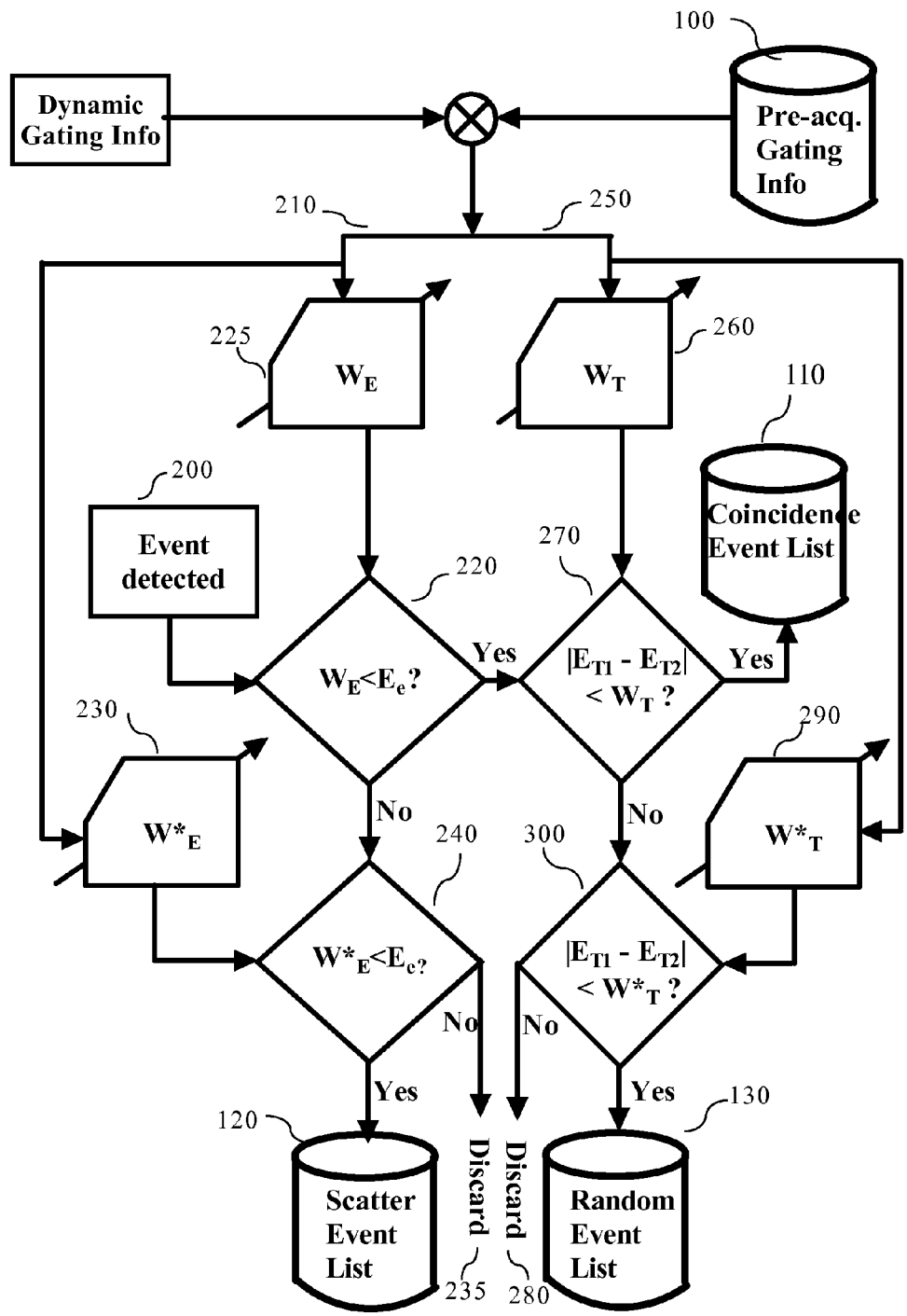
FIG. 4 is a diagram illustrating the data acquisition process with a second set of windowing parameters.

With reference to FIG. 4, a preliminary set of windows determine filtering of spurious events before the events are recorded. All events which pass the preliminary window are stored in list memory 110. Events which do not pass the preliminary set of windows are screened again for use in error analysis. A secondary energy window 240 is employed and if the measured energy of an event 200 exceeds the second window value 230, the event is logged or recorded as a scatter event. For the scatter event list, $W^*_E < E_e$, where $W^*_E$ is the maximum acceptable window energy and $W^*_E < W_E$.

Events 200 which pass through the preliminary energy window 230 and do not pass through the coincidence time window 270 are then passed through a second time window $W^*_T$ 300, where $W_T < W^*_T$ and if the pair passes the second time window 300 is logged or recorded in a separate list as a random event 130 for error analysis.

Figure 5:
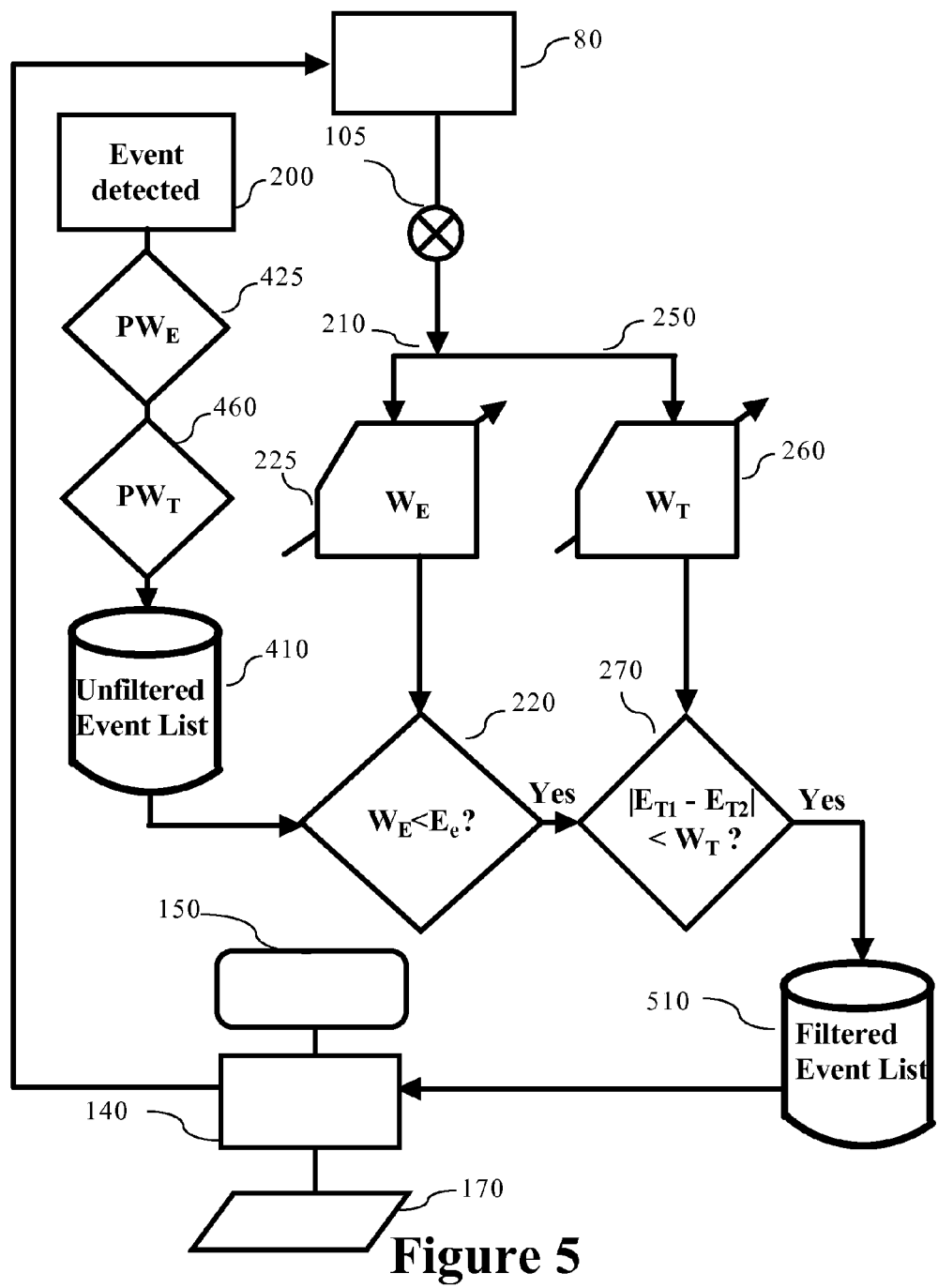
FIG. 5 is a diagram illustrating off-line discrimination tailoring.

With reference to FIG. 5, in a retrospective embodiment, the detected events are stored in an unfiltered list memory 410. In one embodiment, preliminary filtering is performed with a preliminary energy window 425 and a preliminary time window 460. The preliminary energy window keeps events with an energy in a range useable for reconstruction under at least some circumstances, e.g. lowest possible acceptable energy. The preliminary time window represents the widest possible time window that might be selected, e.g. 8 nanoseconds. This separates the scattered events and random events from coincident pairs under the most likable definition coincident pairs.

Bed position, elapsed time since injection of the radiopharmaceutical, temperature, and other information to be used for dynamic windowing are stored in the event list 410.

More restrictive, 225, 220; 260, 270 windowing is performed after acquisition. For reconstruction, the coincidence processing unit 80 adjusts the window parameters in accordance to table position, and the like as described above, e.g. from the system matrix. The restrictively windowed events are stored or buffered in a memory 510 and used by the reconstruction processor to restrict the image. Based on the reconstructed image, the coincidence processor 80 readjusts the energy window 225, 220 and/or the time window 260, 270 and repeats the reconstruction.

The energy window and the time window, in one embodiment, change with region of the patient. For example, LORs that pass through a region of the subject with high count rates can be subject to more restrictive windows and LORS which pass through regions with low count rates can be subject to wider, less restrictive windows.

Figure 6:
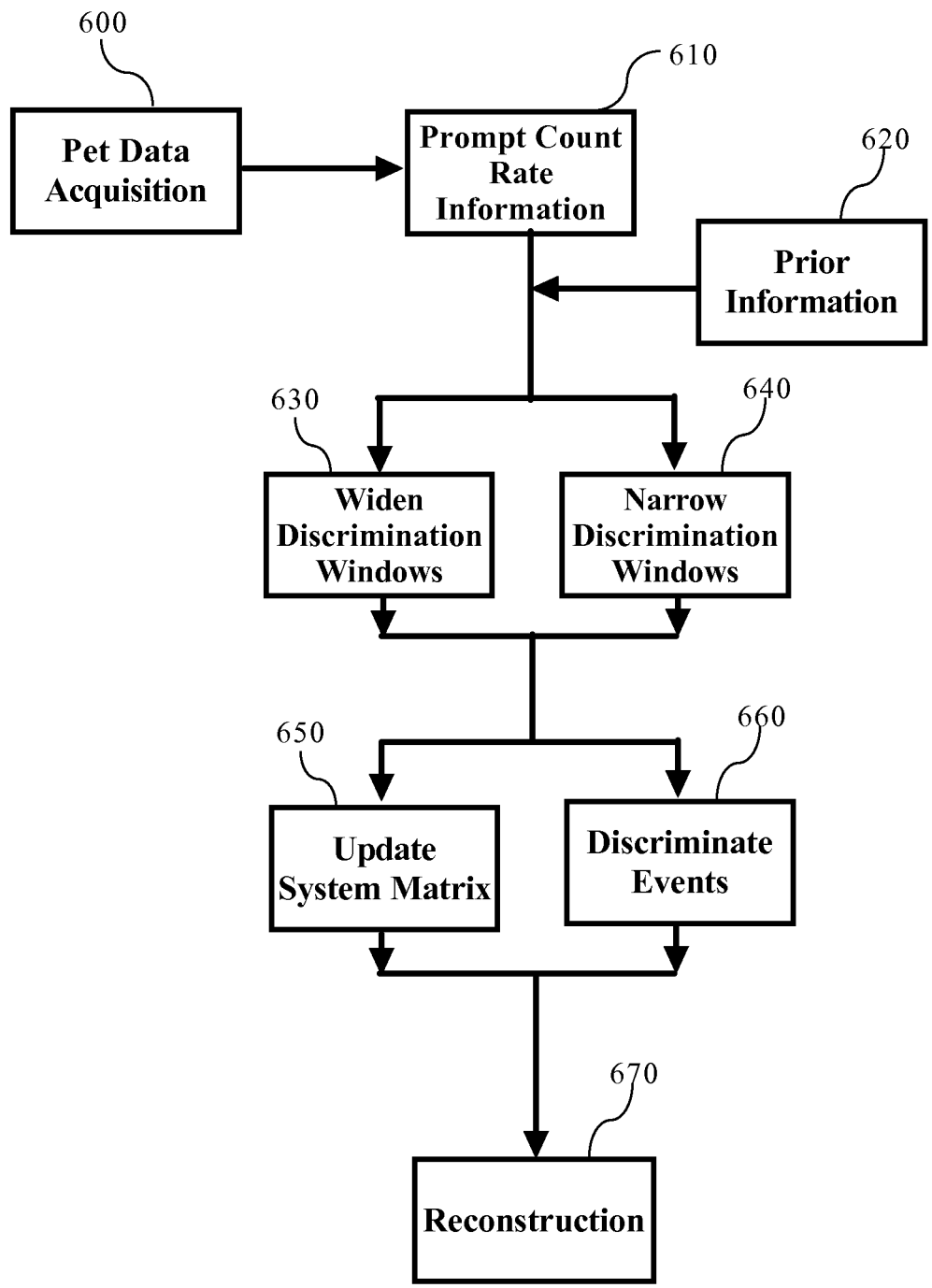
FIG. 6 is a diagram illustrating a method of PET imaging.

With reference to FIG. 6, a diagram illustrates an embodiment of PET imaging. An occurrence of radiation is detected 600 during data acquisition. Count rate information 610 and prior information 620 determined from the acquired data are used to adjust the energy and time windows. The energy and time discrimination windows are widened 630 when for example the count rate in a particular region is low. The discrimination windows are narrowed 640 when for example count rates in a particular region is high. High count rates use computing resources and do not necessarily further add to the quality of an image. Windows are adjusted when the processor determines from the attenuation map that a LOR is likely a scattered event. Events are discriminated 660 based on the window settings. The system matrix that describes the operating parameters of the imaging system is updated 650 with changes. The changes are recorded to reflect changes in windowing parameters when each detection event is acquired 600. Discriminated events 660 are contained in an event list memory 110, 510 which is input to the image reconstruction. The system matrix relates changes in bed position, temperature, duration since rejection of the radiopharmaceutical and the like, and changes in the energy and time windows. Image reconstruction 670 can commence as soon as data is available in an event list memory or as directed by the imaging system.

The invention has been described with reference to the preferred embodiments. Modifications and alterations may occur to others upon reading and understanding the preceding detailed description. It is intended that the invention be con-

Having thus described the preferred embodiments, the invention is now claimed to be:

1. An imaging system comprising:
an array of radiation detectors which performs a data acquisition by detecting radiation events;
a coincidence processor connected with detectors of the array of radiation detectors by wiring circuits, the coincidence processor dynamically adjusting at least one of an energy window and a time window based on feedback about the data acquisition obtained during the data acquisition and selecting the detected events satisfying the dynamically adjusted energy and time windows to define coincident pairs of events;
a list memory which records the coincident event pairs; and
a reconstruction processor which reconstructs the coincident pairs into an image representation.

2. The system according to claim 1, wherein the coincidence processor includes:
a counting circuit which counts the current rate of radiation events;
wherein the coincidence processor dynamically adjusts energy and time windows regionally or globally based on a current count rate.

3. The system according to claim 1, wherein the coincidence processor dynamically adjusts at least one of the time window and the energy window using at least one of:
a current operating temperature of the array of radiation detectors; and
a shift in a maximum energy of detected events.

4. The system according to claim 1 wherein the list memory records at least one of:
time of the event;
detector of the event;
energy of the event; and
window settings and/or system matrix updates.

5. The system according to claim 1 wherein the list memory records at least one of:
table position;
temperature; and
current count rate.

6. The system according to claim 1 wherein the coincidence processor applies preliminary energy and time windows which eliminate scattered and random detected events before the selecting the detected events that satisfy the dynamically adjusted energy and time windows to define the coincident pairs of events.

7. The system according to claim 1 wherein the coincidence processor is programmed to determine a likelihood that each coincident event pair includes scattered radiation, and dynamically adjusts at least one of the energy window and the time window based on the determined likelihood.

8. The system according to claim 1 wherein the coincidence processor determines scattered events and random events as well as the coincident events with the dynamically adjusted energy and time windows.

9. A positron emission tomography (PET) imaging device comprising:
an array of radiation detectors configured to perform a data acquisition including detecting radiation events and adding time stamps to generate detected events; and
a processor connected with detectors of the array of radiation detectors by wiring circuits and configured to perform a coincident events detection and image reconstruction method including:
dynamically adjusting a coincidence pair selection window set comprising an energy window and a time window over the data acquisition based on feedback about the data acquisition obtained during the data acquisition;
identifying coincident pairs as pairs of detected events that satisfy the dynamically adjusted coincidence pair selection window; and
reconstructing the coincident pairs into an image representation.

10. The PET imaging device of claim 9 wherein the dynamic adjusting includes:
dynamically adjusting the coincidence pair selection window set over the data acquisition based on feedback comprising the current rate at which the array of radiation detectors generates detected events.

11. The PET imaging device of claim 10 wherein the dynamic adjusting includes:
widening the energy window and the time window when the current rate is low; and
narrowing the energy window and the time window when the current rate is high.

12. The PET imaging device of claim 9 wherein the dynamic adjusting includes:
dynamically adjusting the coincidence pair selection window set over the data acquisition based on feedback comprising current operating temperature of the array of radiation detectors.

13. The PET imaging device of claim 9 wherein the dynamic adjusting includes:
dynamically adjusting the coincidence pair selection window set over the data acquisition based on feedback comprising a shift in the maximum energy of events.

14. The PET imaging device of claim 9 further comprising:
an unfiltered list memory, wherein:
the data acquisition further includes storing an event list of the detected events in the unfiltered list memory and storing information comprising feedback about the data acquisition received during the data acquisition in the unfiltered event memory, and
the coincident events detection and image reconstruction method is performed retrospectively after the performing of the data acquisition and operates on the event list stored in the unfiltered list memory.

15. A positron emission tomography (PET) imaging device comprising:
an array of radiation detectors configured to Perform a data acquisition including detecting radiation events and adding time stamps to generate detected events;
one or more temperature sensors mounted on the array of radiation detectors; and
a processor connected with detectors of the array of radiation detectors by wiring circuits and configured to perform a coincident events detection and image reconstruction method including:
dynamically adjusting a coincidence pair selection window set comprising an energy window and a time window over the data acquisition based at least on a current operating temperature of the array of radiation detectors measured by the one or more temperature sensors;
identifying coincident pairs as pairs of detected events that satisfy the dynamically adjusted coincidence pair selection window; and
reconstructing the coincident pairs into an image representation.

* * * * *